United States Patent
Bao (10) Patent No.: US 12,157,111 B2
(45) Date of Patent: Dec. 3, 2024

(54) METAL OXIDES FOR SELECTIVE HYDROGEN COMBUSTION

(71) Applicant: ExxonMobil Chemical Patents Inc., Baytown, TX (US)

(72) Inventor: Xiaoying Bao, Houston, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 221 days.

(21) Appl. No.: 17/628,465

(22) PCT Filed: Jul. 30, 2020

(86) PCT No.: PCT/US2020/044184
§ 371 (c)(1),
(2) Date: Jan. 19, 2022

(87) PCT Pub. No.: WO2021/025938
PCT Pub. Date: Feb. 11, 2021

(65) Prior Publication Data
US 2022/0250040 A1    Aug. 11, 2022

Related U.S. Application Data

(60) Provisional application No. 62/882,180, filed on Aug. 2, 2019.

(30) Foreign Application Priority Data

Sep. 25, 2019 (EP) .................................... 19199545

(51) Int. Cl.
*C07C 5/48* (2006.01)
*B01J 23/34* (2006.01)
(Continued)

(52) U.S. Cl.
CPC ............... *B01J 23/75* (2013.01); *B01J 23/34* (2013.01); *B01J 23/745* (2013.01); *C07C 5/48* (2013.01);
(Continued)

(58) Field of Classification Search
CPC . B01J 23/30; B01J 23/34; B01J 23/745; B01J 23/75; B01J 23/78; B01J 23/92;
(Continued)

(56) References Cited

U.S. PATENT DOCUMENTS 5,530,171 A   6/1996  Agaskar et al.
7,338,549 B2  3/2008  Bülow et al.
(Continued)

FOREIGN PATENT DOCUMENTS

WO    2018/049389 A1    3/2018
WO    2018/232133 A1    12/2018
(Continued)

OTHER PUBLICATIONS

Gartner et al. ("Highly Selective Supported Alkali Chloride Catalysts for the Oxidative Dehydrogenation of Ethane." Top Catal (2014) 57:1236-1247) (Year: 2014).*
(Continued)

*Primary Examiner* — In Suk C Bullock
*Assistant Examiner* — Jason Y Chong (57) ABSTRACT

Metal oxides are provided that have selective hydrogen combustion activity while also acting as solid oxygen carriers (SOCs). The metal oxides correspond to a metal oxide core of at least one metal having multiple oxidation states that is modified with an alkali metal oxide and/or alkali metal halogen (such as an alkali metal chloride). The resulting modified metal oxide, corresponding to a solid oxygen carrier, can allow for selective combustion of hydrogen while reducing or minimizing combustion of hydrocarbons,
(Continued)

such as within a propane dehydrogenation environment. Additionally, it has been unexpectedly found that modifying the core metal oxide with the alkali metal oxide and/or alkali metal chloride can also mitigate coke formation on the solid oxygen carrier. Methods of using such metal oxides for selective hydrogen combustion are also provided.

15 Claims, 5 Drawing Sheets

(51) Int. Cl.
   *B01J 23/745* (2006.01)
   *B01J 23/75* (2006.01)
   B01J 23/72 (2006.01)
   B01J 23/755 (2006.01)

(52) U.S. Cl.
   CPC .... *C07C 2523/34* (2013.01); *C07C 2523/745* (2013.01); *C07C 2523/75* (2013.01)

(58) Field of Classification Search
   CPC . B01J 23/94; B01J 27/10; B01J 27/128; B01J 29/44; B01J 35/023; B01J 38/02; B01J 38/12; C07C 5/42; C07C 5/48; C07C 2523/04; C07C 2523/30; C07C 2523/34; C07C 2523/745; C07C 2523/75; C07C 2521/10; C07C 2527/10; C07C 2529/44; Y02P 20/52; Y02P 20/584
   See application file for complete search history.

(56) References Cited

U.S. PATENT DOCUMENTS

| | | |
|---|---|---|
| 2011/0300060 A1 | 12/2011 | Guillou et al. |
| 2016/0318828 A1 | 11/2016 | Washburn et al. |
| 2018/0191031 A1 | 7/2018 | Yu et al. |
| 2019/0055178 A1 | 2/2019 | Weiss et al. |
| 2020/0009539 A1 | 1/2020 | Li et al. |

FOREIGN PATENT DOCUMENTS

| | | |
|---|---|---|
| WO | 2020/046898 A1 | 3/2020 |
| WO | 2020/046978 A1 | 3/2020 |
| WO | 2021/025938 A1 | 2/2021 |

OTHER PUBLICATIONS

Yusuf et al. ("Mixed iron-manganese oxides as redox catalysts for chemical looping-oxidative dehydrogenation of ethane with tailorable heat of reactions." Applied Catalysis B: Environmental 257 (2019): 117885) (Year: 2019).*

Wang et al. ("Oxidative Dehydrogenation of Ethane Over Zirconia-Supported Lithium Chloride Catalysts." Chem. Eng. Technol. 23 (2000) 12: 1041-1126 (Year: 2000).*

* cited by examiner

% O Depletion

METAL OXIDES FOR SELECTIVE HYDROGEN COMBUSTION

CROSS-REFERENCE TO RELATED APPLICATIONS

This application is a US national phase application of PCT Application Serial No. PCT/US2020/044184 having a filing date of Jul. 30, 2020, which claims priority to and the benefit of U.S. Provisional Application No. 62/882,180 having a filing date of Aug. 2, 2019 and European Patent Application No. 19199545.5 having a filing date of Sep. 25, 2019, the disclosures of all of which are incorporated herein by reference in their entireties.

FIELD

Solid oxygen carriers and corresponding methods of using such solid oxygen carriers are provided for selective combustion of hydrogen in the presence of hydrocarbons.

BACKGROUND

Many industrially important chemical conversion processes such as alkane dehydrogenation, catalytic reforming, and alkane dehydrocyclization, are strongly endothermic and equilibrium-limited. In order to enhance equilibrium conversion, low operating pressures, feed dilution, or high operating temperatures are often employed. Unfortunately, modifying the operating conditions to move the equilibrium point can also introduce extra operating costs, undesirable side reactions, and the potential for increased catalyst deactivation. Another option for improving equilibrium yield can be to add supplemental catalysts or supplemental metal oxide particles to the reaction system. This can correspond to using a stacked bed with alternating layers of dehydrogenation catalyst and the supplemental catalyst/metal oxide, a mixture of the dehydrogenation catalyst and the supplemental catalyst/metal oxide, and/or a staged reactor design with alternating dehydrogenation reactors and the supplement catalyst/metal oxide reactors. The supplemental catalyst and/or supplemental metal oxide can be used to combust $H_2$ that is produced during the reaction processes.

An example of a supplemental metal oxide can correspond to a metal oxide with multiple redox states that can also release lattice oxygen at the relevant reaction conditions. $H_2$ that is produced during the processes may be combusted through the lattice oxygen in the metal oxides that have multiple redox states. Such metal oxides can be referred to as solid oxygen carriers (SOCs). Unfortunately, conventional metal oxides that can serve as SOCs usually suffer from low combustion selectivity ($H_2$ vs. hydrocarbon), low hydrogen combustion activity, high cost, and/or or low regenerability. What is needed is an improved metal oxide that can serve as a solid oxygen carrier while also providing one or more of improved combustion selectivity, high hydrogen combustion activity, low cost, and/or improved recyclability.

International Publication Number WO 2018/049389 describes redox catalysts based on a core/shell structure, with a mixed metal oxide core that serves as an oxygen carrier and an outer shell corresponding to a second type of metal oxide to improve activity and/or selectivity. The mixed metal oxide core can have a structure corresponding to a perovskite or a defected rock salt structure. Optionally, the redox catalyst can be used in conjunction with a non-oxidative dehydrogenation catalyst. The metal oxide(s) in the outer shell and the metal oxides of the oxygen carrier core can be present in a molar ratio of 0.5 to 2.5.

U.S. Patent Application Publication 2016/0318828 describes a process for catalytic alkane dehydrogenation. The catalyst system includes an alkane dehydrogenation component and a solid oxygen carrier. Perovskites are described as an example of a suitable solid oxygen carrier with hydrogen combustion activity.

SUMMARY

In an aspect, a solid oxygen carrier for selective hydrogen combustion is provided. The solid oxygen carrier can include 10 wt % or more of at least one first row transition metal oxide comprising multiple redox states. The solid oxygen carrier can further include one or more alkali metal salts comprising at least one of an alkali metal oxide and an alkali metal halide, a molar ratio of the at least one transition metal to the alkali metal in the catalyst being from 0.5 to 100. Additionally, the solid oxygen carrier can have an oxygen storage capacity of 0.5 wt % or more. Optionally, the one or more alkali metal salts can correspond to potassium oxide, potassium chloride, a mixture of potassium oxide and/or potassium chloride with lithium oxide and/or lithium chloride, or a combination thereof.

Optionally, the solid oxygen carrier can be included in a catalyst system. In a catalyst system, the solid oxygen carrier can be included with a dehydrogenation catalyst, a dehydrocyclization catalyst, a reforming catalyst, or a combination thereof.

In another aspect, a hydrocarbon conversion process is provided. The hydrocarbon conversion process can include contacting a hydrocarbon-containing feed with a catalyst system comprising a solid oxygen carrier under effective conditions to form a conversion effluent. The effective conditions being effective for conversion of at least a portion of the hydrocarbon-containing feed to generate hydrogen. In such an aspect, the solid oxygen carrier can include 10 wt % or more of at least one transition metal oxide comprising multiple redox states. The solid oxygen carrier can further include one or more alkali metal salts comprising at least one of an alkali metal oxide and an alkali metal halide, a molar ratio of the at least one transition metal to the alkali metal in the catalyst being from 0.5 to 100. Additionally, the solid oxygen carrier can have an oxygen storage capacity of 0.5 wt % or more.

DETAILED DESCRIPTION

Overview

In various aspects and embodiments, metal oxides are provided that have selective hydrogen combustion activity while also acting as solid oxygen carriers (SOCs). The metal oxides correspond to a metal oxide core of at least one metal having multiple oxidation states that is modified with an alkali metal oxide and/or alkali metal halogen (such as an alkali metal chloride). The at least one metal having multiple oxidation states can also release lattice oxygen under conditions for selective hydrogen combustion. The resulting modified metal oxide, corresponding to a solid oxygen carrier, can allow for selective combustion of hydrogen while reducing or minimizing combustion of hydrocarbons, such as within a propane dehydrogenation environment. Additionally, it has been unexpectedly found that modifying the core metal oxide with the alkali metal oxide and/or alkali metal chloride can also mitigate coke formation on the solid oxygen carrier. Methods of using such metal oxides for selective hydrogen combustion are also provided.

Alkane dehydrogenation, such as propane dehydrogenation, is an example of a process where in-situ hydrogen formation creates difficulties. Alkane dehydrogenation can be used, for example, to form olefins for use as polymer feedstock. Unfortunately, the alkane dehydrogenation reaction is an equilibrium process, so the hydrogen generated by converting an alkane to an alkene can potentially convert an alkene back to an alkane. Due to this equilibrium, the alkene yield from alkane dehydrogenation is limited relative to the alkane content of the feed. More generally, examples of endothermic processes that generate in-situ hydrogen include, but are not limited to, processes based on exposing a hydrocarbon-containing feed to a dehydrogenation catalyst, a dehydrocyclization catalyst, a reforming catalyst, or a combination thereof.

Using a metal oxide corresponding to a solid oxygen carrier with activity for hydrogen combustion is potentially an attractive solution for increasing the yield from reactions such as alkane dehydrogenation. Such a co-catalyst can be provided in the form of separate catalyst particles or can be composited with the catalyst that has the dehydrogenation activity. Unfortunately, use of such hydrogen combustion catalysts pose a variety of challenges. Some challenges relate to providing a combination of selectivity for hydrogen combustion with high activity for hydrogen combustion. While combustion of hydrogen is desirable, it is also desirable to reduce or minimize combustion of the alkenes, alkanes, and/or any other hydrocarbons present in the reaction environment. Many solid oxygen carriers can catalyze combustion but lack selectivity, so that hydrocarbons in the reaction environment are also converted to $CO_2$. Such non-selective combustion catalysts provide little or no yield improvement, as any yield increases from removing hydrogen from the reaction environment are offset by yield losses due to combustion of the desired reactants and/or reaction products. Conversely, some solid oxygen carriers with high selectivity also have minimal activity for hydrogen combustion, so that little or no benefit is realized.

Another challenge with solid oxygen carriers is regenerability. During use, a solid oxygen carrier is cycled between different redox states in order to provide lattice oxygen for $H_2$ combustion and to replenish the lattice oxygen. During such redox cycles, the solid oxygen carrier should not lose available lattice oxygen for $H_2$ combustion. For example, bismuth oxide based materials are an example of a potential solid oxygen carrier. Unfortunately, the reduced state of bismuth, bismuth metal, has a low melting point of 271° C. Due to this low boiling point, the reduced bismuth metal can tend to melt during a redox cycle, which leads loss of bismuth dispersion and available oxygen for hydrogen combustion.

It has been discovered that the selectivity for hydrogen combustion and/or the regenerability of solid oxygen carriers can be improved in propane dehydrogenation environments when an alkali metal oxide and/or alkali metal halide is added to the solid oxygen carrier. In particular, oxides and chlorides where the alkali metal is potassium or potassium plus lithium have been found to provide an unexpectedly beneficial combination of selectivity for hydrogen combustion and regenerability.

In some aspects, the solid oxygen carriers can correspond to any convenient type of solid oxygen carrier. Thus, the solid oxygen carrier can generally include one or more metal oxides, where at least one metal oxide in the solid oxygen carrier has a plurality of oxidation states. The at least one metal oxide with the plurality of oxidation states serves as the oxygen source for the selective hydrogen combustion, and any oxygen lost from the at least one metal oxide is replaced during regeneration. Examples of suitable metal oxides can include transition metal oxides with multiple redox states, such as first row transition metal oxides.

In other aspects, the solid oxygen carriers can correspond to oxides of single metals that are modified to have activity for selective hydrogen combustion. The single metal oxide core can correspond to an oxide of a transition metal that has multiple redox states (i.e., a metal from columns 3-12 of the periodic table). In some aspects, the single metal can correspond to a first row transition metal selected from Mn, Fe, Co, Ni, Cu, and/or another first row transition metal that has multiple redox states.

In some aspects, the metal oxide with multiple redox states can be impregnated, coated, or otherwise modified with one or more alkali metal oxides and/or alkali metal halides, such as $K_2O$, KCl, a mixture of $K_2O$ and KCl, or a mixture including at least one of $K_2O$ and KCl and at least one of $Li_2O$ and LiCl. In some aspects, a molar ratio of the metal in the single metal oxide to the alkali metal can range from roughly 0.1 to 100, or 0.5 to 100, or 0.1 to 50, or 0.5 to 50, or 0.1 to 10, or 0.5 to 10, or 0.1 to 1.0, or 1.0 to 10, or 0.5 to 5.0.

In this discussion, the term "single metal oxide" refers to an oxide that can be identified spectroscopically as including oxide phases corresponding to a single metal. For example, an oxide containing phases corresponding to iron (II) oxide and iron (III) oxide corresponds to a single metal oxide. This is in contrast to a mixed metal oxide, where at least a portion of the crystalline phases correspond to phases where two or more metals are present within a crystalline phase. The mole percentage of single metal oxide phases versus mixed metal oxide phases can be determined based on X-ray diffraction.

The term "hydrocarbon" means (i) any compound consisting of hydrogen and carbon atoms or (ii) any mixture of two or more such compounds in (i). The term "$C_n$ hydrocarbon," where n is a positive integer, means (i) any hydrocarbon compound comprising carbon atom(s) in its molecule at the total number of n, or (ii) any mixture of two or more such hydrocarbon compounds in (i). Thus, a $C_2$ hydrocarbon can be ethane, ethylene, acetylene, or mixtures of at least two of them at any proportion. A "$C_m$ to $C_n$ hydrocarbon" or "$C_m$-$C_n$ hydrocarbon," where m and n are positive integers and m<n, means any of $C_m$, $C_m+1$, $C_m+2$, ..., $C_{n-1}$, $C_n$ hydrocarbons, or any mixtures of two or more thereof. Thus, a "$C_2$ to $C_3$ hydrocarbon" or "$C_2$-$C_3$ hydrocarbon" can be any of ethane, ethylene, acetylene, propane, propene, propyne, propadiene, cyclopropane, and any mixtures of two or more thereof at any proportion between and among the components. A "saturated $C_2$-$C_3$ hydrocarbon" can be ethane, propane, cyclopropane, or any mixture thereof of two or more thereof at any proportion. A "$C_{n+}$ hydrocarbon" means (i) any hydrocarbon compound comprising carbon atom(s) in its molecule at the total number of at least n, or (ii) any mixture of two or more such hydrocarbon compounds in (i). A "$C_{n-}$ hydrocarbon" means (i) any hydrocarbon compound comprising carbon atoms in its molecule at the total number of at most n, or (ii) any mixture of two or more such hydrocarbon compounds in (i). A "$C_m$ hydrocarbon stream" means a hydrocarbon stream consisting essentially of $C_m$ hydrocarbon(s). A "$C_m$-$C_n$ hydrocarbon stream" means a hydrocarbon stream consisting essentially of $C_m$-$C_n$ hydrocarbon(s).

The term "aromatic" as used herein is to be understood in accordance with its art-recognized scope which includes alkyl substituted and unsubstituted mono- and polynuclear compounds.

The phrases, unless otherwise specified, "consists essentially of" and "consisting essentially of" do not exclude the presence of other steps, elements, or materials, whether or not, specifically mentioned in this specification, so long as such steps, elements, or materials, do not affect the basic and novel characteristics of this disclosure. Additionally, they do not exclude impurities and variances normally associated with the elements and materials used. "Consisting essentially of" a component in this disclosure can mean, e.g., comprising, by weight, at least 80 wt %, of the given material, based on the total weight of the composition comprising the component.

In this discussion, references to groups of elements correspond to groups according to the IUPAC Periodic Table. Thus, Group 10 metals include Ni, Pt, and Pd. In this discussion, transition metals are defined as metals corresponding to atomic numbers 21 to 30, 39-48, 57, and 72-80. In this discussion, first row transition metals are defined as metals with atomic numbers of 21 to 30.

Solid Oxygen Carrier Composition

In various aspects, metal oxides described herein correspond to solid oxygen carriers with selective hydrogen combustion activity. The metal oxides include a core composed of one or more metal oxides that have multiple redox states, where the core is modified by one or more alkali metal oxides and/or alkali metal halides. The metal oxides can correspond to transition metal oxides, such as first row transition metal oxides.

In some aspects, the solid oxygen carrier can include a core composed of single metal oxides. A solid oxygen carrier including a core composed of single metal oxides is defined herein as a catalyst where 50 wt % or more of the transition metal oxides in the catalyst correspond to single metal oxides, or 60 wt % or more, or 70 wt %, such as up to 100 wt % (i.e., such as up to substantially all transition metal oxides in the catalyst being single metal oxides). Optionally but preferably, the transition metal oxides can be first row transition metal oxides (atomic numbers 21-30). In some aspects, the (first row) transition metal oxides can correspond to oxides of Mn, Fe, Co, Ni, and/or Cu. In such aspects, 10 wt % or more (or 30 wt % or more, or 50 wt % or more, such as up to 75 wt %) of the metal oxides in the catalyst can correspond to single metal oxides of Mn, Fe, Co, Ni, and/or Cu. In some aspects, the single metal oxides can be oxides of Mn and/or Fe. Single metal oxides are in contrast to mixed metal oxides. It is noted that the different oxidation states of the single metal may be present in the core, such as having both $Fe_2O_3$, $Fe_3O_4$, and FeO present in the core, as well as potentially some reduced metal (Fe). It is further noted that mixtures of the first row transition metal oxides can be present in the single metal oxide core, so long as the X-ray diffraction (or other detection method) shows that the oxides are present as single metal oxide phases, and not as mixed metal oxide phases.

In addition to the transition metal core, the metal oxide with selective hydrogen combustion activity can include an alkali metal oxide and/or alkali metal halide (such as an alkali metal chloride). The alkali metal oxide and/or alkali metal halide can provide improved selectivity for hydrogen combustion. For example, metal oxides based on Mn, Fe, Co, Ni, and/or Cu can provide non-selective combustion activity, so that both hydrogen and hydrocarbons are combusted. Modification of such metal oxides with an alkali metal oxide and/or alkali metal halide can provide an unexpected improvement in selectivity for hydrogen combustion, while also providing an unexpected improvement in regenerability.

In some aspects, a single alkali metal oxide or alkali metal halide can be used, while in other aspects a mixture of alkali metal oxides and/or alkali metal halides can be used. Examples of alkali metal oxides and alkali metal chlorides generally include $Li_2O$, $Na_2O$, $K_2O$, LiCl, NaCl, and mixtures of $Li_2O$, $Na_2O$, and $K_2O$, LiCl, NaCl, and KCl. In some aspects, it has been discovered that alkali metal oxides and/or alkali metal chlorides based on potassium ($K_2O$, KCl) or a combination of potassium and lithium can provide unexpectedly beneficial selectivity in a propane dehydrogenation environment. When a mixture of alkali metals is used, the molar ratio of a first alkali metal to a second alkali metal can be from 0.1 to 10.

The molar ratio of transition metal (metal oxide core) to alkali metal (alkali metal oxide and/or alkali metal halide) can be a ratio that provides a desired level of hydrogen combustion activity while also providing high selectivity for hydrogen combustion relative to hydrocarbon combustion. Depending on the aspect, the molar ratio of transition metal to alkali metal is 10 or less, or 8.0 or less, or 6.0 or less, or 4.0 or less. For example, the molar ratio of first row transition metal to alkali metal can be from 10 to 0.1, or 10 to 1.0, or 10 to 2.0, or 8.0 to 0.1, or 8.0 to 1.0, or 8.0 to 2.0, or 6.0 to 0.1, or 6.0 to 1.0, or 6.0 to 2.0, or 4.0 to 0.1, or 4.0 to 1.0, or 4.0 to 2.0. Having too little alkali metal can result in insufficient selectivity for hydrogen combustion. Having too much alkali metal can result in too little activity for hydrogen combustion.

The resulting solid oxygen carrier can have an oxygen storage capacity. It has been unexpectedly discovered that addition of alkali metal oxide and/or alkali metal chloride can increase the oxygen storage capacity of the catalyst. In this discussion, the oxygen storage capacity is expressed relative to the weight of transition metal oxides in the solid oxygen carrier. In various aspects, the oxygen storage capacity of the solid oxygen carrier can be 0.5 wt % or more, or 2.0 wt % or more, or 5.0 wt % or more, such as up to 10 wt % or possibly still higher. Additionally or alternatively, the increase in oxygen storage capacity, relative to the oxygen storage capacity of the metal oxide without modification by the alkali metal oxide and/or halide, can be 1.0 wt % or more. Without being bound by any particular theory, it is believed that modifying the catalyst with the alkali metal oxide and/or halide can reduce or mitigate the impact of coke formation on the oxygen storage capacity.

The solid oxygen carrier can be formed by a variety of methods. One option is addition of alkali metal salt to the metal oxide core by wet impregnation. For example, a powder of (first row) transition metal oxide can be formed by any convenient method for formation of particles in the size range of 0.001 μm to 100 μm, or 0.01 μm to 20 μm, or 0.05 μm to 100 μm, or 0.05 μm to 20 μm. For the alkali metal oxide or alkali metal chloride, the alkali metal precursor (such as KCl) is dissolved in deionized water. The powder of the transition metal oxide is then added to the solution of the alkali metal precursor and stirred until the metal oxide powder is completely wet. The water is then evaporated to leave behind the alkali metal salt modified powder which corresponds to the catalyst. Optionally, the catalyst can be calcined after removing the water.

Other methods for forming the solid oxygen carrier (i.e., other methods modifying the single metal oxide core with the alkali metal salt) include incipient wetness impregnation and solid state mixing.

During use, the solid oxygen carrier can be used to selectively combust hydrogen while having a reduced or minimized amount of combustion of hydrocarbons. The selectivity can be characterized in various ways. In this discussion, selectivity is characterized based on selectivity for a feed containing hydrogen, propane, and propene, where the molar ratio of hydrogen to propene is from 0.95 and 1.05 and the molar ratio of hydrogen to propane is from 0.75 and 0.85. The feed can optionally further include $N_2$ or a noble gas. The feed is exposed to the catalyst at a temperature of roughly 540° C., a pressure of ~0 kPa-g, and a weight hourly space velocity of 0.5 $hr^{-1}$. The space velocity is calculated based on weight of the propane and propene versus the weight of the solid oxygen carrier. Optionally, the solid oxygen carrier can be mixed with inert/diluent particles that are not included in the space velocity calculation.

The selectivity is determined based on the moles of $H_2$ that are converted versus the moles of propane and propene that are converted in the presence of the catalyst. One option for characterizing the selectivity is based on the minimum selectivity at any time during the exposure of the feed to the catalyst. The minimum selectivity can occur at the beginning of the exposure, or it may occur shortly after the beginning of the exposure. The minimum selectivity can be 50% or more, or 65% or more, or 80% or more, such as up to 100% selectivity (i.e., no activity for hydrocarbon combustion). Another option can be to characterize the selectivity at 50% of the oxygen storage capacity. The selectivity at 50% of the oxygen storage capacity can be 75% or more, or 85% or more, such as up to 100% selectivity.

Performing combustion using the solid oxygen carrier results in depletion of oxygen in the metal oxide. The oxygen "vacancies" in the metal oxide can be replaced by regenerating the catalyst in the presence of oxygen under regeneration conditions. Regeneration can be performed by exposing the solid oxygen carrier to an oxygen-containing feed (such as air) at a regeneration temperature of 400° C. to 1000° C.

In some aspects, the solid oxygen carrier can be used in combination with one or more catalysts as part of a catalyst system. In such aspects, the solid oxygen carrier and the catalysts can be included in the catalyst system in any convenient manner. For example, the solid oxygen carrier and one or more catalysts can be included in the form of stacked beds and/or staged beds, where a catalyst in the catalyst system is in a first bed and the solid oxygen carrier is in a second bed. Additionally or alternatively, solid oxygen carrier particles and particles of one or more catalysts can form a mixture of particles as at least part of a catalyst system. Still another option can be to formulate particles that include both a catalyst and the solid oxygen carrier.

Processing Conditions Example—Propane Dehydrogenation

The processing conditions for using the solid oxygen carrier can vary depending on the type of process that is desired. Propane dehydrogenation is an example of a process that can benefit from using a solid oxygen carrier with activity for selective hydrogen combustion. The solid oxygen carrier can be included as separate particles in a physical mixture with the catalyst for propane dehydrogenation, or a composite catalyst can be formed that includes both the propane dehydrogenation catalyst and the solid oxygen carrier. The relative amount of the propane dehydrogenation catalyst (and/or other dehydrogenation catalyst) and the solid oxygen carrier is selected to achieve the specified functions. For example, the solid oxygen carrier can correspond to 10 wt % or more, or 2.0 wt % or more or 30 wt % or more of the combined weight of dehydrogenation catalyst and solid oxygen carrier, such as up to 50 wt % or possibly still higher.

Any convenient type of alkane dehydrogenation catalyst can be used. Examples of catalysts suitable for propane dehydrogenation can include mixed metal catalysts.

The alkane dehydrogenation catalyst can include at least one material having alkane dehydrogenation functionality, particularly non-oxidative alkane dehydrogenation functionality. This functionality can be provided by at least one metal selected from Groups 5-14 of the Periodic Table, including such metals in oxide and/or sulfide form. The alkane dehydrogenation catalyst can further include at least one additional material utilized as binder, matrix, and/or support. Typically, such additional materials include one or more inorganic oxides or sulfides, such as those that are stable under process conditions specified for dehydrogenation, combustion, and re-oxidation. For example, the additional material can include one or more inorganic oxides of elements in Groups 13 and 14 of the Periodic Table, silica and/or alumina.

The dehydrogenation functionality can be provided by one or more of (i) Group 5 metals including V, Nb and Ta, with V being preferred, (ii) Group 6 metals including Cr, Mo, W with Cr and Mo being preferred, and Cr being particularly preferred, (iii) Group 7 metals including Mn and Re, with Mn being preferred, (iv) Group 8 metals including Fe, Ru and Os, with Fe being preferred, (v) Group 9 metals including Co, Rh and Ir, with Co being preferred, (vi) Group 10 metals including Ni, Pd and Pt, with Ni and Pt being preferred, and Pt being particularly preferred, (vii) Group 11 metals including Cu, Ag and Au, with Cu being preferred, (viii) Group 12 metals including Zn and Cd, with Zn being preferred, (ix) Group 13 metals including Al, Ga, In and Tl, with Ga and In being preferred, and (x) Group 14 metals including Ge, Sn and Pb, with Sn being preferred.

An alkane dehydrogenation reaction can be performed in a reaction zone. The reaction zone is typically located in a reactor, such as a tube reactor. A plurality of reactors can be used, e.g., a plurality of reactors arranged in series, parallel, or series parallel. Typically, the reaction zone is substantially isothermal at the start of the process, but this is not required since isothermal conditions can be established during the course of the dehydrogenation reaction in dehydrogenation mode. Dehydrogenation mode typically operates for a first time interval, during which a flow of a first feed, an alkane-containing feed, is established into the reaction zone. At least a portion of the first feed's alkane is dehydrogenated in the presence of a catalytically effective amount of a propane dehydrogenation catalyst, as well as an amount of the selective hydrogen combustion catalyst that is effective for combustion of at least a portion of the hydrogen generated during the dehydrogenation reaction. The propane dehydrogenation catalyst and the selective hydrogen combustion catalyst can be present as a mixture of separate catalyst particles, or as a composite particles including both types of catalyst. During dehydrogenation mode, the reaction zone is maintained under isothermal conditions, typically by adding or removing heat from reaction zone components, feed or components thereof, and/or reaction product or components thereof. At least a portion of the molecular hydrogen in the dehydrogenation product is combusted in the reaction zone in the presence of an oxidant that is associated with (e.g., stored in or stored on) the selective hydrogen combustion catalyst. Combustion of the molecular hydrogen with the stored oxidant produces water in the reaction product, which can be separated from the reaction product, e.g., downstream of the reaction zone, such as by one or more of fractionation, extraction, gravitational settling, etc. Dehydrogenation mode is typically carried out until (i) alkane conversion (indicated by an increase in unreacted alkane in the reaction product) is 90% or less of the amount of conversion at the start of dehydrogenation mode, or 75% or less, or 50% or less; and/or (ii) selectivity for the desired olefin (indicated by the amount of desired olefin in the reaction product) is 90% or less of the amount of selectivity at the start of dehydrogenation mode, or 75% or less, or 50% or less. Typically, when this occurs, the flow of the alkane-containing feed stream through the reaction zone is curtailed or ceased, so that regeneration mode can be carried out. The first time interval can correspond to 1.0 seconds to 10 hours, or possibly more.

Regeneration mode typically includes replenishing at least a portion of the oxidant in the selective hydrogen combustion catalyst that was consumed during dehydrogenation mode and removing at least a portion of the accumulated coke on dehydrogenation catalyst and/or the selective hydrogen combustion catalyst. Regeneration mode is typically carried out during a second time interval. After oxidation, the selective hydrogen combustion catalyst can be used again during the next reaction cycle for selective hydrogen combustion. It is noted that regeneration may not fully restore the oxygen storage capacity of the selective hydrogen combustion catalyst.

In an alternative aspect, regeneration mode is not carried out within the reactor. In such cases, spent selective hydrogen combustion catalyst is removed from the reaction zone and replaced with fresh or regenerated material. Replacement can be carried out continuously, e.g., utilizing conventional fluidized catalyst or slurry catalyst technology, in a batch method, and in combinations thereof.

The reaction zone can be substantially isothermal during the second time interval, but this is not required. At least a portion of the second feed's oxidant, typically oxygen, is stored by the active materials' oxidant storage sites. The second feed's oxidant is also used for removing coke deposits from catalysts within the reaction zone. Once sufficient re-oxidation has occurred, i.e., sufficient oxidant is stored to carry out the molecular hydrogen combustion during dehydrogenation mode, the flow of the second feed through the reaction zone can be curtailed or ceased, and the flow of first feed re-established. Regeneration mode can be carried out for a sufficient time to (i) replenish 20 wt % or of the SOC's original oxidant storage capacity, or 50 wt % or more, or 75 wt % or more, or 90 wt % or more, such as up to substantially all of the original oxygen storage capacity; and/or (ii) remove 50 wt % or more of accumulated coke on the catalyst(s), such as up to removal of substantially all accumulated coke. Generally, the duration of regeneration mode is 300% or less of the duration of dehydrogenation mode, or 100% or less, or 50% or less, or 25% or less.

Alternating flows of first and second feeds, e.g., alternating first and second time intervals can be repeated continuously or semi-continuously. One or more additional feeds, e.g., one or more sweep fluids, can be utilized between flows of the first and second feeds, e.g., to remove undesired material from the reactors, such as non-combustible particulates including soot. The additional feeds are typically inert under conditions specified for the first and second time intervals.

The reaction zone can include one or more fixed bed reactors containing the same or different catalysts, a moving bed reactor, or a fluidized bed reactor. The feeds may be contacted with the active material in one or more of an upward, downward, or radial flow fashion. The feeds and reaction product removed from the reaction zone may be in the liquid phase, mixed liquid and vapor phase, or typically in the vapor phase. Typically a fixed bed reactor is employed, e.g., one having a plurality of beds of one or more of the specified active materials. When the reaction zone contains a plurality of beds of active material, the active material of each bed can be of the same composition (e.g., using the same type and amount of dehydrogenation component and solid oxygen carrier), but this is not required.

During dehydrogenation mode, the reaction zone is maintained or controlled to have a substantially isothermal temperature profile at about the reaction zone's average temperature. In one aspect the reaction zone's average temperature is in a range of from 400° C. to 700° C. Alternatively, the reaction zone's average temperature is in a range of from 450° C. to 650° C., or in a range of from 400° C. to 600° C. In another alternative embodiment, the reaction zone's average temperature is in a range of from 400° C. to 500° C. It is observed that a lower average temperature in the reaction zone, e.g., in the range of from 400° C. to 500° C., increases yield of the desired olefin and decreases the yield of undesired by products such as methane. Optionally, the reaction zone can be controlled, e.g., to exhibit a temperature profile having a variance from the average temperature of +/−10° C. or less during dehydrogenation mode.

During the dehydrogenation mode, the reaction zone is maintained or controlled at a pressure effective for carrying out the specified dehydrogenation and molecular hydrogen combustion reactions. In certain aspects, the reaction zone pressure is ≥0 psia (0 kPa·a) and ≤500 psia (3447 kPa·a). Alternatively, the reaction zone pressure is in a range of from 5 psia (34 kPa·a) to 200 psia. (1379 kPa·a) or in a range of from 10 psia. (69 kPa·a) to 100 psia. (689 kPa·a) or in a range of from 15 psia (103 kPa·a) to 50 psia (344 kPa·a). The flow of alkane-containing feed into the reaction zone is carried out to achieve a weight hourly space velocity (WHSV) effective for carrying out the catalytic dehydrogenation process. In one embodiment, the WHSV is from 0.1 hr$^{-1}$ to 100 hr$^{-1}$. Alternatively, the WHSV is from 0.5 hr$^{-1}$ to 50 hr$^1$.

Example 1—Mn$_3$O$_4$ Modified with Various Salts

An example of a solid oxygen carrier is Mn$_3$O$_4$. Without modification, Mn$_3$O$_4$ has low selectivity for preferentially combusting hydrogen versus combusting of hydrocarbons. In an effort to identify solid oxygen carriers with improved selectivity, Mn$_3$O$_4$ particles were modified with various coatings or layers.

The solid oxygen carriers with various coatings or layers are shown in Table 2. Each of the solid oxygen carriers in Table 2 was exposed to a feed under conditions representative of propane dehydrogenation conditions in a pilot scale reactor. In the reactor, the solid oxygen carrier was mixed with silicon carbide, which served as an inert diluent.

The solid oxygen carriers (SOCs) were exposed to a feed under conditions representative of propane dehydrogenation conditions in a pilot scale reactor. The feed was a model feed believed to be representative of reaction products from a propane dehydrogenation reaction. Additional details of the feed and the reaction conditions are shown in Table 1.

TABLE 1

Process Parameters for Mn$_3$O$_4$ Catalysts

| Pressure | | ~1 atm (~101 kPa) (absolute) |
|---|---|---|
| Temperature | | 540° C. |
| Feed | H$_2$ | 27 |
| Composition | C$_3$H$_8$ | 35 |
| (mol %) | C$_3$H$_6$ | 27 |
| | Ar | 10 |

At t<0, the SOC/diluent mixture was heated up to the reaction temperatures under He. A mixed H$_2$/C$_3$H$_8$/C$_3$H$_6$/Ar (27/35/27/10) gas was flown though the bypass and their concentrations were monitored using an Agilent microGC 490 equipped with columns that detect CO, CH$_4$, Ar, C$_3$H$_8$, C$_3$H$_6$, C$_2$H$_4$, C$_2$H$_6$, CO$_2$, He, H$_2$, N$_2$. At t>0, the valve located at the upstream of the reactor switched and the mixed gas flew through the solids, sweeping the small amounts of He in the reactor out and started reaction. The void spaces in the reactor was packed with quartz chips to minimize the dead volume in the reactor.

Table 2 shows the carbon balance, hydrogen flow rate and CO$_2$ flow rate in ml/min right after the reaction started. The ratio between the H$_2$ flow rate and the total feed flow rate in terms of percentage is denoted as R1, the ratio between the initial CO$_2$ flow rate and the total feed flow rate in terms of percentage is denoted as R2. Low R1/R2 and high C balance indicates good performance. A carbon balance of less than 90% is an indication of severe coke formation.

As shown in Table 2, Mn$_3$O$_4$ without a promoter had a low R1 value but a high R2 value. This indicates that Mn$_3$O$_4$ without a promoter was effective for hydrogen combustion, but at the cost of also oxidizing a substantial amount of hydrocarbon.

For the alkali metal chlorides, LiCl and NaCl resulted in substantially increased amounts of CO$_2$ formation. Thus, addition of just LiCl or just NaCl appeared to be less suitable than Mn$_3$O$_4$ alone as a solid oxygen carrier for selective hydrogen combustion. By contrast, addition of KCl substantially lowered the R2 value, indicating that a reduced or minimized amount of CO$_2$ was formed. Although the R1 value is increased, indicating less than full combustion of all hydrogen, the low R2 value indicates a high selectivity for hydrogen combustion. Similar but potentially higher selectivity results were observed for mixtures of LiCl and KCl.

For the alkali metal oxides, the R2 values were relatively low, indicating low production of CO$_2$. However, the carbon balance was comparatively lower for the metal oxides shown in Table 2, indicating substantial coke formation and therefore a lower selectivity for hydrogen combustion than the alkali metal chlorides.

TABLE 2

Hydrogenation Selectivity for Mn$_3$O$_4$ Based Solid Oxygen Carriers

| SOC description | SOC mass (g) | Feed flow rate (ml/min) | Initial H$_2$ flow rate (ml/min) | R1 (%) | Initial CO$_2$ flow rate (ml/min) | R2 (%) | C balance (%) | Notes |
|---|---|---|---|---|---|---|---|---|
| Mn$_3$O$_4$ | 4.00 | 60 | 1.89 | 3.2 | 9.32 | 15.5 | 95 | |
| KCl/LiCl 3:0.2:0.3 | 4.49 | 60 | 6.59 | 11.0 | 2.54 | 4.2 | 100 | |
| KCl/LiCl 3:0.5:0.75 | 5.23 | 60 | 12.66 | 21.1 | 0.03 | 0.1 | 98 | |
| LiCl 3:1.25 | 4.92 | 60 | 0.96 | 1.6 | 38.2 | 63.7 | Not measured | |
| NaCl 3:1.25 | 5.28 | 60 | 0.50 | 0.8 | 30.9 | 51.5 | Not measured | |
| KCl 3:1.25 | 5.69 | 60 | 10.65 | 17.8 | 0.10 | 0.2 | 97 | Cokes after O depletes |
| Na$_2$O 3:1.25 | 1.56 | 20 | 0.11 | 0.6 | 0.03 | 0.2 | 88 | |
| Na$_2$O/K$_2$O 3:1:0.25 | 4.75 | 60 | 0.55 | 0.9 | 3.20 | 5.3 | 85 | |
| MgO 3:1.25 | 4.88 | 60 | 1.49 | 2.5 | 9.15 | 15.3 | 96 | |
| Na$_2$WO$_4$ 3:1.25 | 5.00 | 41 | 11.1 | 27.0 | 0 | 0 | 100 | No activity |

For the additional promoters, magnesium oxide had poor selectivity, as indicated by the high R2 value (high CO$_2$ production). Sodium tungstate resulted in no activity for either hydrogen combustion or hydrocarbon conversion. Thus, even though sodium tungstate had little or no carbon conversion, the selectivity for hydrogen combustion was minimal.

Additional characterization was also performed for the $Mn_3O_4$ solid oxygen carrier and for two solid oxygen carriers including a combination of LiCl and KCl. The $Mn_3O_4$ particles had an average particle size of roughly 2.0 µm to 8.0 µm. One of the solid oxygen carriers including both LiCl and KCl had a molar ratio of Mn to K to Li of 3.0:0.2:0.3. Thus, the molar ratio of first row transition metal to alkali metal for the second solid oxygen carrier was roughly 6.0. The other solid oxygen carrier including both LiCl and KCl had a molar ratio of Mn to K to Li of 3.0:0.5:0.75. Thus, the molar ratio of first row transition metal to alkali metal for the third solid oxygen carrier was roughly 2.4.

Figure 1:
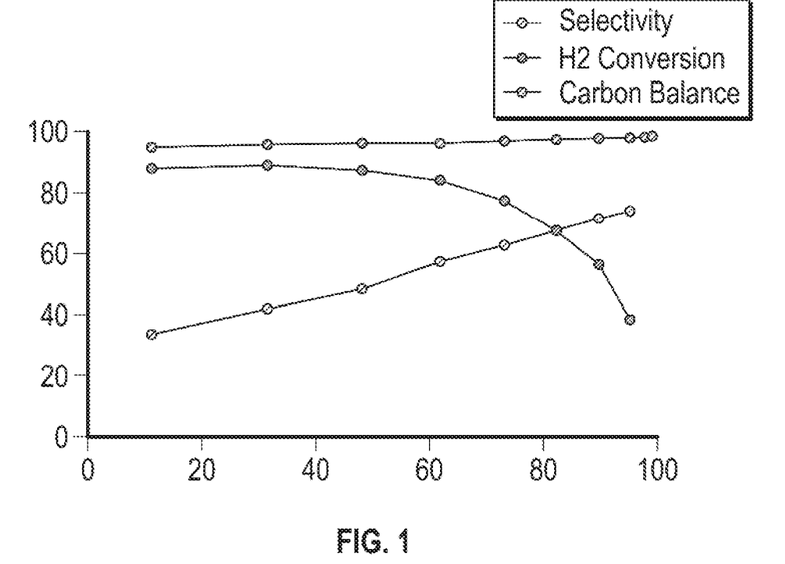
FIG. 1 shows results from exposing a model feed to a comparative solid oxygen carrier for selective hydrogen combustion.

FIG. 1 shows results from exposing the feed to the first solid oxygen carrier, which corresponded to just $Mn_3O_4$ particles. In FIG. 1, $H_2$ conversion, selectivity, and carbon balance are shown relative to the portion of the oxygen storage capacity that has been used. For the first SOC ($Mn_3O_4$), the oxygen storage capacity was determined to be 5.4 wt %. The values shown in FIG. 1 were determined based on gas chromatograph analysis of the products.

As shown in FIG. 1, the $Mn_3O_4$ particles initially provided nearly complete combustion of hydrogen, but with a selectivity for combustion of hydrogen of less than 40%. This corresponds to the profile of non-selective combustion, as both hydrogen and hydrocarbons are combusted in significant amounts. The selectivity slowly increased as the oxygen storage capacity was depleted, but was still less than 50% after 50% of the oxygen storage capacity was consumed. After roughly 60% of the oxygen storage capacity was consumed, the activity for hydrogen combustion started to decline corresponding to a decrease in activity for hydrogen combustion.

Figure 2:
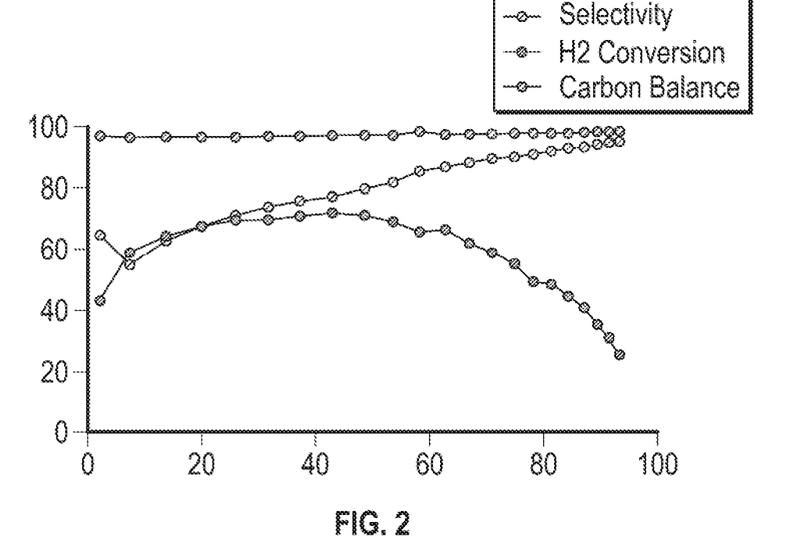
FIG. 2 shows results from exposing a model feed to a solid oxygen carrier for selective hydrogen combustion.

FIG. 2 shows results from using the second solid oxygen carrier, where the molar ratio of Mn:K:Li was 3.0:0.2:0.3. As shown in FIG. 2, modifying the solid oxygen carrier with alkali metal resulted in a substantial increase in selectivity, with the selectivity being greater than 50% at all times during the reaction. Based on the substantially greater amount of hydrocarbon present in the feed, a selectivity of greater than 50% represents activity for selective hydrogen combustion. Additionally, the modified solid oxygen carrier has an unexpectedly increased oxygen capacity of 7.5 wt %, thus allowing for longer reaction time prior to requiring regeneration. It is noted that at 50% consumption of the oxygen storage capacity, the second solid oxygen carrier provides the favorable combination of greater than 60% selectivity and greater than 70% hydrogen conversion.

Figure 3:
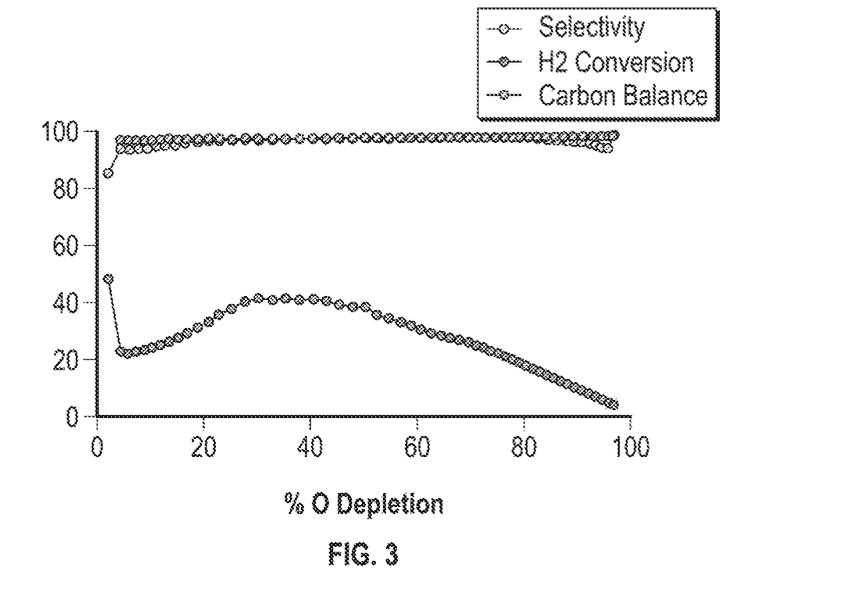
FIG. 3 shows results from exposing a model feed to a solid oxygen carrier for selective hydrogen combustion.

FIG. 3 shows that addition of greater amounts of alkali metal to the solid oxygen carrier results in still further improvements in selectivity. For the third solid oxygen carrier, with a molar ratio of Mn:K:Li of 3.0:0.5:0.75, the selectivity is greater than 90% at all times. Although the hydrogen conversion is lower, the high selectivity means that hydrogen can be selectively combusted with little or no loss of hydrocarbons. This type of selectivity can allow for a shifting of equilibrium for a dehydrogenation reaction with little or no loss of the desired dehydrogenation product. The oxygen storage capacity for the third solid oxygen carrier was 7.2 wt %, which is comparable to the oxygen storage capacity for the second solid oxygen carrier.

Example 2—$Fe_2O_3$ Modified with Alkali Metal Salts

Another example of a solid oxygen carrier is $Fe_2O_3$ as a single metal oxide that is modified with a coating. Table 3 shows results from testing various iron oxide based solid oxygen carriers. The iron oxide based solid oxygen carriers were tested in a manner similar to the $Mn_3O_4$ solid oxygen carriers in Example 1.

TABLE 3

Hydrogenation Selectivity for $Fe_2O_3$ Based Solid Oxygen Carriers

| SOC description | SOC mass (g) | Feed flow rate (ml/min) | Initial $H_2$ flow rate (ml/min) | R1 (%) | Initial $CO_2$ flow rate (ml/min) | R2 (%) | C balance (%) | Notes |
|---|---|---|---|---|---|---|---|---|
| $Fe_2O_3$ | 5.31 | 40 | 1.36 | 3.4 | 29.3 | 73.2 | 75 | |
| $Li_2O/K_2O$ 3:0.5:0.5 | 6.00 | 40 | 1.16 | 2.9 | 0.69 | 1.7 | 97 | |
| $Li_2O/K_2O$ 3:0.75:0.75 | 6.00 | 37.3 | 0.83 | 2.2 | 0.59 | 1.6 | 86 (Subsequent data points have much higher C balance) | |
| $Na_2O$ 3:1 | 6.00 | 18.7 | 0.77 | 4.1 | 0.25 | 1.3 | Not measured | Cokes after O depletes |
| $K_2O$ 3:1 | 6.00 | 37.3 | 1.12 | 3.0 | 0.14 | 0.4 | 98 | Cokes after O depletes |
| KCl 3:1 | 3.48 | 19.9 | 0.80 | 4.0 | 0.36 | 1.8 | 96 | |

As shown in Table 3, $Fe_2O_3$ alone had a high R2 value and a low carbon balance (less than 90%), indicating poor selectivity for hydrogen combustion. Modifying the iron oxide with potassium (either $K_2O$ or KCl) resulted in low R1, low R2, and high carbon balance, indicating high selectivity for hydrogen combustion. Thus, both $K_2O$ and KCl are effective promoters, either alone or in combination. Adding $Li_2O$ to $K_2O$ also resulted in good selectivity. Similar to the modification of $Mn_3O_4$ with $Na_2O$ in Table 2, addition of $Na_2O$ to $Fe_2O_3$ resulted in high hydrogen combustion and low $CO_2$ production.

Additional characterization was also performed for the $Fe_2O_3$ solid oxygen carrier and two solid oxygen carriers including a combination of LiCl and KCl. The $Fe_2O_3$ solid oxygen carrier particles had an average particle size of less than 5.0 μm. The second iron oxide based solid oxygen carrier had a molar ratio of Fe to K to Li of 3.0:0.5:0.5, as shown in Table 3. Thus, the molar ratio of first row transition metal to alkali metal was roughly 3.0. A third iron oxide based solid oxygen carrier was also made by wet impregnation to add a coating of $Li_2O$ and $K_2O$ to the $Fe_2O_3$ particles. These third solid oxygen carrier particles had a molar ratio of Fe to K to Li of 3.0:0.75:0.75. Thus, the molar ratio of first row transition metal to alkali metal was roughly 2.0.

The three solid oxygen carriers were exposed to the model feed from Example 1 under conditions representative of alkane dehydrogenation conditions in a pilot scale reactor. Additional details of the feed and the reaction conditions are shown in Table 4. It is noted that the weight of $Fe_2O_3$ in the solid oxygen carrier particles was constant for testing of each catalyst. Particles of silicon carbide were also included in the reactor loading as a diluent.

TABLE 4

Process Parameters for $Fe_2O_3$ Catalysts

| | | |
|---|---|---|
| Pressure | | ~1 atm (~101 kPa) (absolute) |
| Temperature | | 540° C. |
| Feed | $H_2$ | 27 |
| Composition | $C_3H_8$ | 35 |
| (mol %) | $C_3H_6$ | 27 |
| | Ar | 10 |

Figure 4:
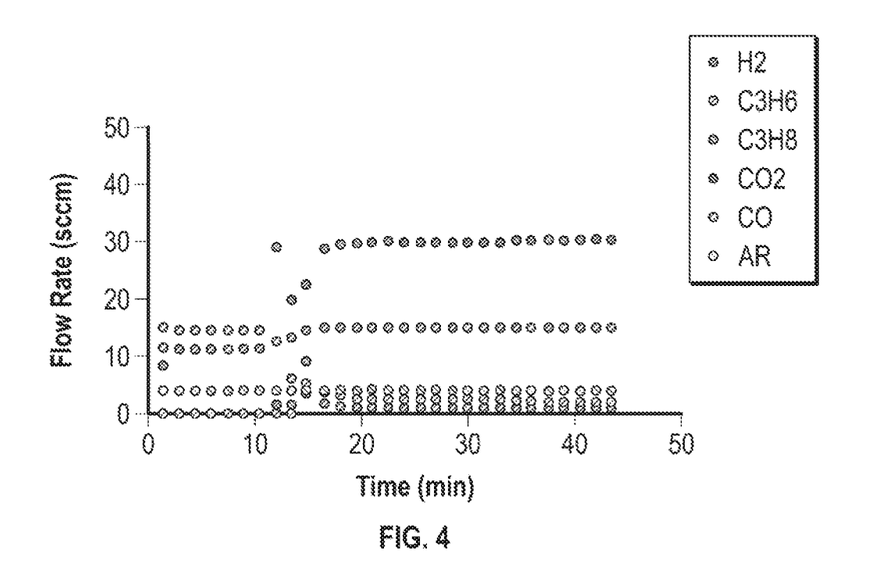
FIG. 4 shows results from exposing a model feed to a comparative solid oxygen carrier for selective hydrogen combustion.

FIG. 4 shows results from exposing the feed to the first solid oxygen carrier, which corresponded to just $Fe_2O_3$ particles. In FIG. 4, the output flows from the reactor are shown, as detected by gas chromatography. The output flow includes the components of the feed as well as CO and $CO_2$ formed due to hydrocarbon combustion. Water generated by combustion is not shown. In FIG. 4, the first 10 minutes of the plot show the feed being bypassed to avoid the catalyst, so that the feed is delivered directly to the microGC. At 10 minutes, the feed flow path is switched so that the feed contacts the catalyst in the reaction zone.

As shown in FIG. 4, the primary activity of $F_2O_3$ is for deep dehydrogenation. When the flow path of the feed is switched to expose the feed to the solid oxygen carrier, an initial amount of both hydrogen combustion and alkane combustion occurs. This results in a temporary spike in $CO_2$ and CO levels, along with some reduction in propane due to combustion. The amount of propene also decreases with a corresponding increase in hydrogen, indicating conversion of propene to carbonaceous compounds. The deep dehydrogenation to form carbonaceous compounds is maintained for the duration of the time shown in FIG. 4. Based on FIG. 4, $Fe_2O_3$ alone has little or no ability to serve as a solid oxygen carrier for selective hydrogen combustion.

Figure 5:
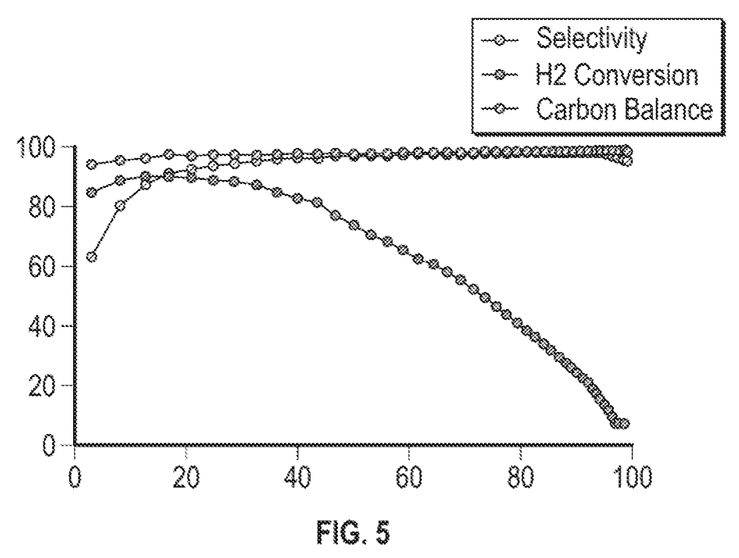
FIG. 5 shows results from exposing a model feed to a solid oxygen carrier for selective hydrogen combustion.

Modification of the $Fe_2O_3$ with alkali metal oxide and/or chloride results in a solid oxygen carrier with a substantially different activity profile. FIG. 5 shows results from using the second solid oxygen carrier, where the molar ratio of Fe:K:Li was 3.0:0.5:0.5. As shown in FIG. 5, modifying the catalyst with alkali metal resulted in activity for selective hydrogen combustion. The second solid oxygen carrier provides greater than 60% selectivity at all times, while also providing greater than 80% hydrogen conversion when the solid oxygen carrier reaches 50% depletion of the stored oxygen. The oxygen storage content for the solid oxygen carrier was 5.3 wt %. The ability for a modest overcoat of alkali metal salt to change the activity of a metal oxide from deep dehydrogenation into selective hydrogen combustion is unexpected.

Figure 6:
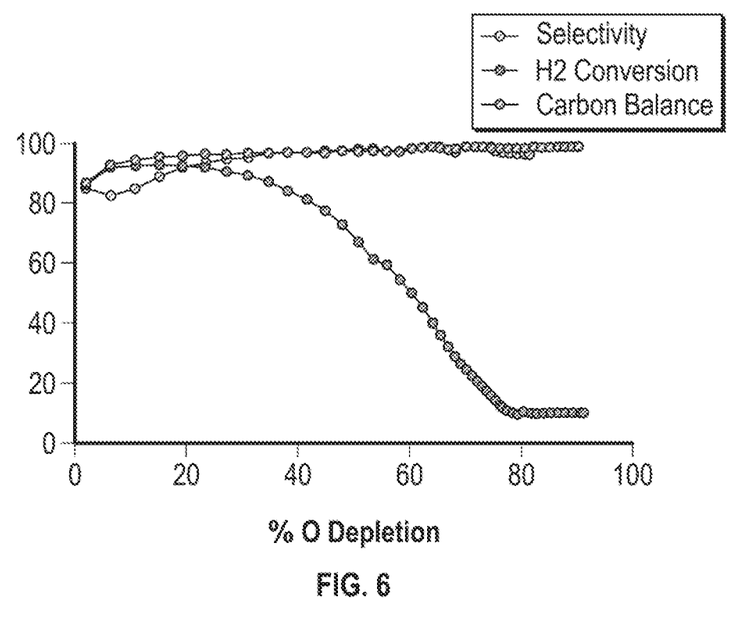
FIG. 6 shows results from exposing a model feed to a solid oxygen carrier for selective hydrogen combustion.

As shown in FIG. 6, the third solid oxygen carrier, with the molar ratio of Fe:K:Li was 3.0:0.75:0.75, is similar in reactivity and selectivity to the second solid oxygen carrier. The selectivity is greater than 80% at all times, and the hydrogen conversion is modestly lower, but otherwise the activity and selectivity profiles are similar to those in FIG. 5. The oxygen storage capacity for the third solid oxygen carrier was 5.4 wt %.

Example 3—Use of Solid Oxygen Carrier for Selective Hydrogen Combustion During Propane Dehydrogenation An iron oxide based solid oxygen carrier described in Example 2 (molar ratio of Fe:K:Li of 3.0:0.75:0.75) was used as part of a catalyst system for propane dehydrogenation. The catalyst system corresponded to 97.5 wt % of the solid oxygen carrier and 2.5 wt % of a propane dehydrogenation catalyst. The propane dehydrogenation catalyst was a conventional catalyst including Pt and Ag supported on ZSM-5.

When testing the combined performance of the propane dehydrogenation catalyst and the solid oxygen carrier, the reactor was heated to 540° C. The catalyst system was then exposed to a feed including 90 mol % $C_3H_8$ and 10 mol % Ar.

Figure 7:
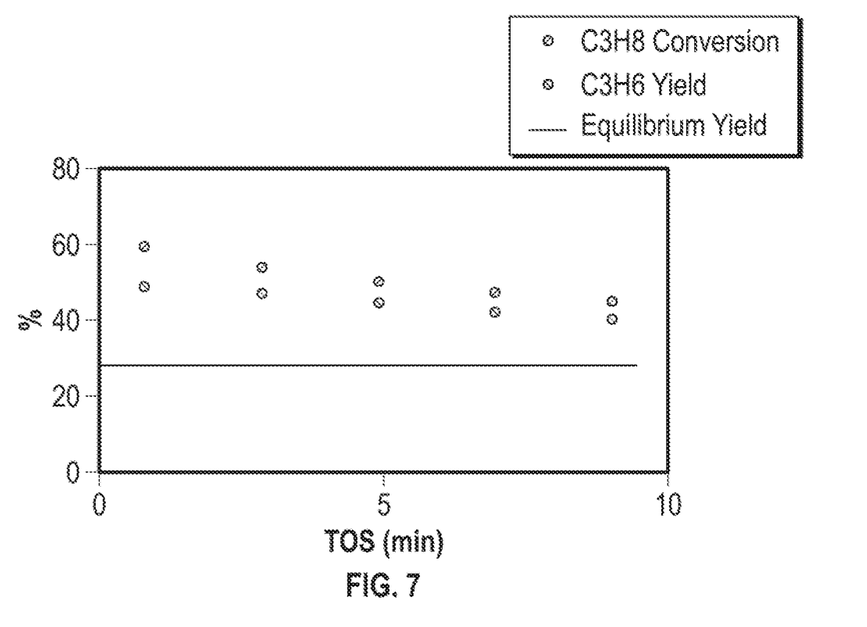
FIG. 7 shows measured propene yield from propane dehydrogenation in the presence of propane dehydrogenation catalyst and a solid oxygen carrier.

FIG. 7 shows the propene yield plotted against time on stream. FIG. 7 also shows the expected equilibrium yield from performing propene dehydrogenation in the presence of only the propane dehydrogenation catalyst. As shown in FIG. 7, including the solid oxygen carrier as part of the catalyst system during propane dehydrogenation resulted in an increase in propene yield of between 10 C % and 25 C %.

Example 4—$Co_3O_4$ Modified with Alkali Metal Salts

Modification of cobalt oxide with alkali metal salts was also investigated for potential use as a solid oxygen carrier during propane dehydrogenation. Table 3 shows the results from use of $Co_3O_4$ by itself, or after modification with a mixture of $Li_2O$ and $K_2O$.

TABLE 3

Hydrogenation Selectivity for $Fe_2O_3$ Based Solid Oxygen Carriers

| SOC description | SOC mass (g) | Feed flow rate (ml/min) | Initial $H_2$ flow rate (ml/min) | R1 (%) | Initial $CO_2$ flow rate (ml/min) | R2 (%) | C balance (%) |
|---|---|---|---|---|---|---|---|
| $Co_3O_4$ | 4.00 | 60 | 0.18 | 0.3 | 33.7 | 56 | 63% |
| $Li_2O/K_2O$ 3:0.5:0.5 | 4.00 | 60 | 0.40 | 0.7 | 19.4 | 32 | 105% |

As shown in Table 5, exposure of $Co_3O_4$ to the model feed results in both high $CO_2$ formation and low carbon balance, indicating poor selectivity for hydrogen combustion. Addition of a mixture of $Li_2O$ and $K_2O$ results in an improved carbon balance, indicating a reduction in coke formation. However, selectivity is still low due to high $CO_2$ production.

Comparative Example 6—Solid Oxygen Carriers for Ethane Cracking

It has been discovered that selectivity in a propane dehydrogenation environment does not correlate directly with selectivity in other similar environments, such as an ethane cracking environment. To demonstrate this, two of the solid oxygen carriers described in Examples 1 and 2 were exposed to a model feed under ethane cracking conditions. One of the solid oxygen carriers was $Fe_2O_3$ modified with both $Li_2O$ and $K_2O$, which was the highest selectivity combination shown in Examples 1 and 2. The other solid oxygen carrier exposed to the ethane cracking model feed was $Mn_3O_4$ modified with sodium tungstate, which resulted in no activity at all under propane dehydrogenation conditions. Additionally, a blank run was performed by exposing just quartz chips to the ethane cracking model feed.

Figure 8:
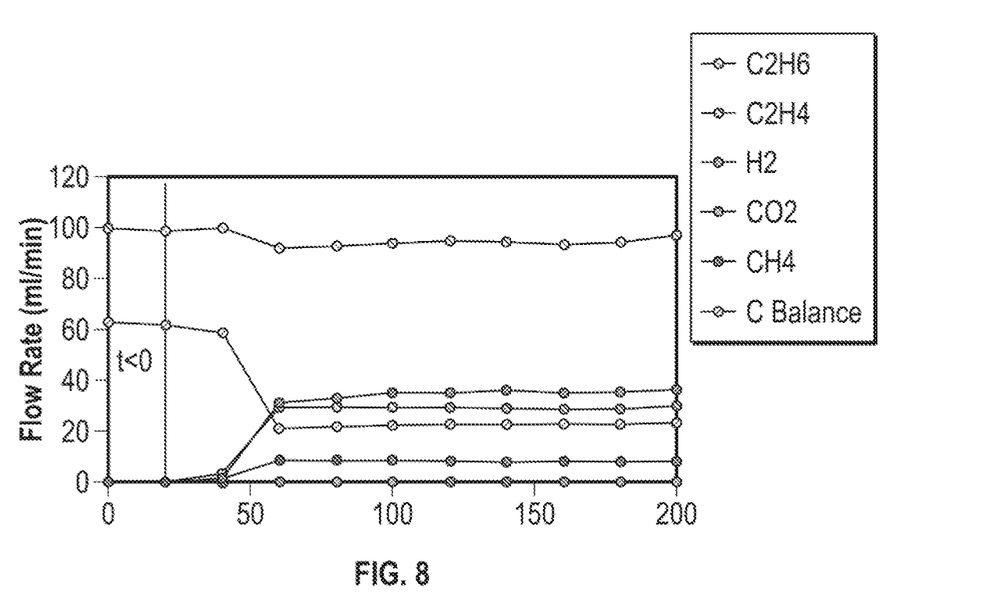
FIG. 8 shows results from exposing a model ethane cracking feed to quartz chip under ethane cracking conditions.
Figure 9:
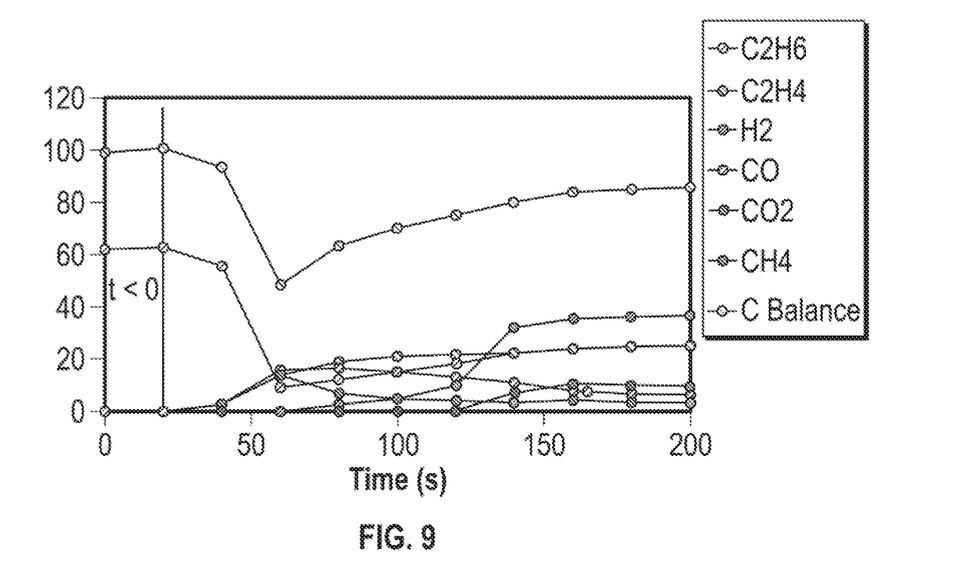
FIG. 9 shows results from exposing a model ethane cracking feed to a solid oxygen carrier under ethane cracking conditions.
Figure 10:
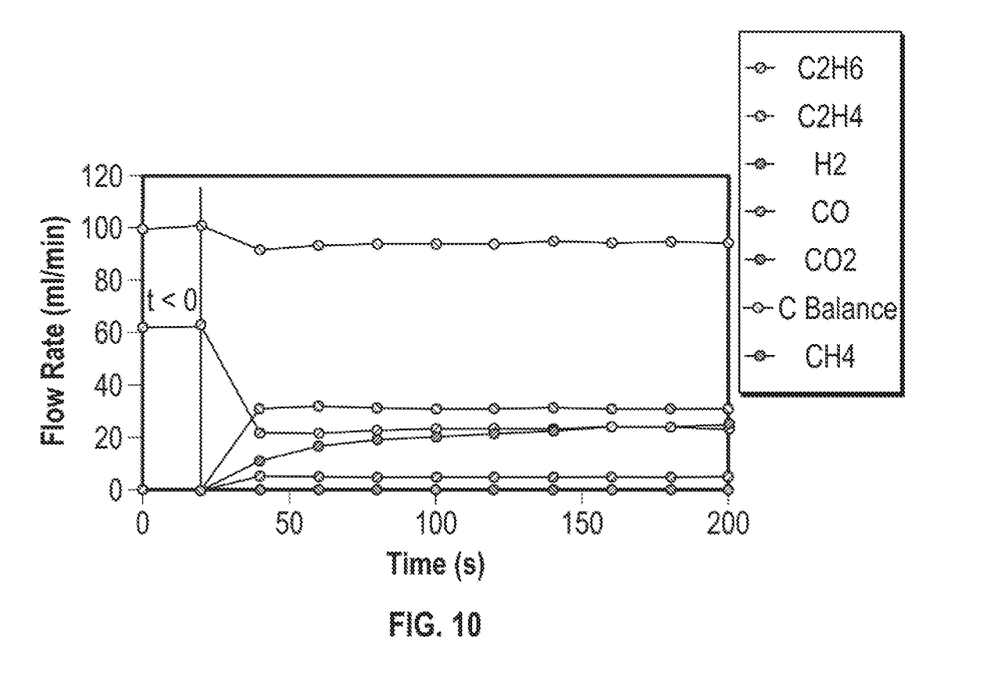
FIG. 10 shows results from exposing a model ethane cracking feed to a solid oxygen carrier under ethane cracking conditions.

A gas consisting of 90% $C_2H_6$ and 10% Kr as the internal standard was used as the feed. The flow rate of the feed was 70 ml/min (20° C., 1 atm). The ethane cracking reaction conditions included a temperature of 800° C. at ambient pressure. FIGS. 8-10 show the flow rates of $C_2H_6$, $C_2H_4$, $H_2$, CO and $CO_2$ before and after the ethane cracking/selective $H_2$ combustion reaction.

FIG. 8 shows the baseline scenario when the quartz reactor was filled with quartz chips. As shown in FIG. 8, the reaction conditions were effective for dehydrogenation of ethane to form ethylene and $H_2$.

FIG. 9 shows results from performing the ethane cracking in the presence of $Li_2O/K_2O$ promoted $Fe_2O_3$ (Fe:K:Li=3:0.75:0.75). The $Li_2O/K_2O$ promoted $Fe_2O_3$ provided an unexpected combination of high selectivity for $H_2$ combustion with low hydrocarbon conversion for the simulated propane dehydrogenation exhaust in Example 2. As shown in FIG. 9, there was a period of time (time=20–20 s) when the $H_2$ flow rate was significantly smaller than the $C_2H_4$ flow rate, with concomitant production of $CO_2$. At time >120 s, a significant amount of CO was formed. This demonstrates the unpredictable nature of a propane dehydrogenation environment relative to an ethane cracking environment, as an effective solid oxygen carrier for selective $H_2$ combustion during propane dehydrogenation was substantially less effective for selective $H_2$ combustion during ethane cracking. Without being bound by any particular theory, $K_2O$ is most likely in a molten state at the reaction temperature (800° C.) since its melting point is 740° C. The change of state of $K_2O$ may change the capability of the alkali metal oxide film to differentiate $H_2$ vs hydrocarbon through diffusion, which could explain the poorer performance for selective $H_2$ combustion during ethane cracking. In addition, the $C_2$ molecules may be able diffuse through the alkali metal oxide film and react with lattice oxygen more easily than the $C_3$ molecules, due to the smaller size of the $C_2$ molecules.

The results in FIG. 10 further illustrate the unpredictable differences between a propane dehydrogenation environment and an ethane cracking environment. In FIG. 10, $Na_2WO_4$ promoted $Mn_3O_4$ (Mn:Na=3:1.25) was used as the solid oxygen carrier in the ethane cracking environment. As shown in Example 1, $Na_2WO_4$ promoted $Mn_3O_4$ showed virtually no activity for either $H_2$ or hydrocarbon combustion when tested under propane dehydrogenation conditions. When tested for ethane cracking, however, the $Na_2WO_4$ promoted $Mn_3O_4$ showed activity for selective $H_2$ combustion with almost no production of $CO/CO_2$. $Na_2WO_4$ has a melting point of 700° C., and therefore may be in a molten state during ethane cracking at 800° C. while being in a solid state during propane dehydrogenation at 540° C. Without being bound by any particular theory, $H_2$ is able to diffuse through the molten $Na_2WO_4$ layer at 800° C. to react with lattice oxygen while it is not able to diffuse through the solid $Na_2WO_4$ layer at 540° C. to react with lattice oxygen.

All numerical values within the detailed description and the claims herein are modified by "about" or "approximately" the indicated value, and take into account experimental error and variations that would be expected by a person having ordinary skill in the art.

While the present disclosure has been described and illustrated with respect to certain embodiments, it is to be understood that the disclosure is not limited to the particulars disclosed and extends to all equivalents within the scope of the claims. Unless otherwise stated, all percentages, parts, ratios, etc. are by weight. Unless otherwise stated, a reference to a compound or component includes the compound or component by itself as well as in combination with other elements, compounds, or components, such as mixtures of compounds. Further, when an amount, concentration, or other value or parameter is given as a list of upper preferable values and lower preferable values, this is to be understood as specifically disclosing all ranges formed form any pair of an upper preferred value and a lower preferred value, regardless of whether ranges are separately disclosed. All patents, test procedures, and other documents cited herein, including priority documents, are fully incorporated by reference to the extent such disclosure is not inconsistent and for all jurisdictions in which such incorporation is permitted.

The invention claimed is:

1. A hydrocarbon conversion process, comprising:
    contacting a hydrocarbon-containing feed with a catalyst system comprising a solid oxygen carrier under effective conditions to form a conversion effluent, the effective conditions being effective for conversion of at least a portion of the hydrocarbon-containing feed to generate hydrogen,
    the solid oxygen carrier comprising:
        10 wt % or more of at least one transition metal oxide comprising multiple redox states; and
        one or more alkali metal salts comprising an alkali metal chloride, a molar ratio of the at least one transition metal to the alkali metal in the solid oxygen carrier being from 0.5 to 10,
        wherein the solid oxygen carrier comprises an oxygen storage capacity of 0.5 wt % or more and
        wherein the at least one transition metal oxide comprises an oxide of Mn, Fe, Co, Ni, Cu, or a combination thereof.

2. The method of claim 1, wherein the alkali metal comprises K or a combination of Li and K.

3. The method of claim 1, wherein the catalyst system further comprises a dehydrogenation catalyst, a dehydrocyclization catalyst, a reforming catalyst, or a combination thereof.

4. The method of claim 1, wherein the alkali metal chloride comprises LiCl, NaCl, KCl, or a mixture thereof.

5. The method of claim 1, wherein the at least one transition metal oxide comprises a single metal oxide.

6. The method of claim 1, wherein the molar ratio of the at least one transition metal to the alkali metal in the solid oxygen carrier is from 0.5 to 8.

7. The method of claim 1, wherein:
the at least one transition metal oxide consists essentially of an oxide of Fe,
70 wt % or more of the oxide of Fe is in the form of a single metal oxide, and
the alkali metal chloride comprises LiCl, KCl, or a mixture thereof.

8. The method of claim 1, wherein:
the hydrocarbon-containing feed comprises a propane-containing feed,
the catalyst system further comprises a propane dehydrogenation catalyst, and
the propane dehydrogenation catalyst comprises Pt.

9. The method of claim 1, wherein the one or more alkali metal salts further comprises an alkali metal oxide.

10. The method of claim 1, wherein the at least one transition metal oxide comprises Mn and the alkali metal chloride comprises LiCl, KCl, or a mixture thereof.

11. The method of claim 1, wherein the at least one transition metal oxide comprises Fe and the alkali metal chloride comprises LiCl, KCl, or a mixture thereof.

12. The method of claim 1, wherein:
the at least one transition metal oxide consists essentially of an oxide of Mn,
the alkali metal chloride consists essentially of KCl or a mixture of KCl and LiCl, and
the molar ratio of the at least one transition metal to the alkali metal in the solid oxygen carrier is from 2.4 to 6.

13. The method of claim 1, wherein:
the at least one transition metal oxide consists essentially of an oxide of Fe, and
the alkali metal chloride consists essentially of KCl or a mixture of KCl and LiCl.

14. The method of claim 1, wherein:
the at least one transition metal oxide consists essentially of an oxide of Mn,
the alkali metal chloride comprises KCl or a mixture of KCl and LiCl,
the molar ratio of the at least one transition metal to the alkali metal in the solid oxygen carrier is from 2.4 to 6,
the hydrocarbon-containing feed comprises a propane-containing feed,
the catalyst system further comprises a propane dehydrogenation catalyst, and
the propane dehydrogenation catalyst comprises Pt.

15. The method of claim 1, wherein:
the at least one transition metal oxide consists essentially of an oxide of Fe,
the alkali metal chloride comprises of KCl or a mixture of KCl and LiCl,
the hydrocarbon-containing feed comprises a propane-containing feed,
the catalyst system further comprises a propane dehydrogenation catalyst, and
the propane dehydrogenation catalyst comprises Pt.

* * * * *